(12) United States Patent
Wall, Jr.

(10) Patent No.: US 11,819,256 B1
(45) Date of Patent: Nov. 21, 2023

(54) METHODS OF INDUCING APOPTOSIS IN TISSUES

(71) Applicant: Simeon Wall, Jr., Shreveport, LA (US)

(72) Inventor: Simeon Wall, Jr., Shreveport, LA (US)

(*) Notice: Subject to any disclaimer, the term of this patent is extended or adjusted under 35 U.S.C. 154(b) by 917 days.

(21) Appl. No.: 16/259,544

(22) Filed: Jan. 28, 2019

Related U.S. Application Data

(63) Continuation of application No. 13/465,499, filed on May 7, 2012, now Pat. No. 10,188,280.

(60) Provisional application No. 61/518,553, filed on May 6, 2011.

(51) Int. Cl.
*A61B 18/02* (2006.01)
*A61B 17/00* (2006.01)
*A61B 18/00* (2006.01)

(52) U.S. Cl.
CPC ........ *A61B 18/02* (2013.01); *A61B 17/00234* (2013.01); *A61B 2018/00005* (2013.01); *A61B 2018/00101* (2013.01); *A61B 2018/00172* (2013.01); *A61B 2018/00244* (2013.01); *A61B 2018/00464* (2013.01); *A61B 2018/0237* (2013.01)

(58) Field of Classification Search
CPC .............. A61B 18/02; A61B 17/00234; A61B 2018/00005; A61B 2018/00101; A61B 2018/00172; A61B 2018/00244; A61B 2018/00464; A61B 2018/0237
See application file for complete search history.

(56) References Cited

U.S. PATENT DOCUMENTS

| | | | | |
|---|---|---|---|---|
| 6,283,959 B1* | 9/2001 | Lalonde | ................. | A61B 18/02 606/23 |
| 6,428,534 B1* | 8/2002 | Joye | ....................... | A61B 18/02 607/105 |
| 6,733,442 B1* | 5/2004 | Larnard | ................. | A61B 17/02 600/203 |
| 6,942,677 B2 | 9/2005 | Nita et al. | | |
| 2005/0090816 A1* | 4/2005 | McClurken | ............ | A61B 17/32 606/49 |
| 2005/0261670 A1* | 11/2005 | Weber | .................... | B82Y 30/00 606/23 |
| 2007/0031338 A1* | 2/2007 | Zabinski | .............. | A61K 31/455 514/355 |
| 2009/0131925 A1* | 5/2009 | Tempel | .............. | A61B 18/1492 606/213 |
| 2010/0100114 A1* | 4/2010 | Berger | ............... | A61B 17/0218 606/191 |
| 2022/0000533 A1* | 1/2022 | Lalonde | ................. | A61B 18/02 |

* cited by examiner

*Primary Examiner* — Jason E Flick
(74) *Attorney, Agent, or Firm* — R. Keith Harrison

(57) ABSTRACT

Methods of inducing apoptosis in a tissue may include providing a tissue separation and equalization device having a generally elongated tissue insertion member, providing an incision in tissue, inserting the tissue insertion member of the tissue separation and equalization device through the incision into the tissue reducing a temperature of the tissue insertion member and removing the tissue insertion member from the tissue.

18 Claims, 12 Drawing Sheets

US 11,819,256 B1

METHODS OF INDUCING APOPTOSIS IN TISSUES

CROSS-REFERENCE TO RELATED APPLICATIONS

This is a continuation of U.S. patent application Ser. no. 13/465,499, filed May 7, 2012 and entitled TISSUE SEPARATION, EQUALIZATION, ERADICATION AND REGENERATION DEVICES AND METHODS, which parent application claims the benefit of U.S. provisional application no. 61/518,533, filed May 6, 2011 and entitled TISSUE SEPARATION AND EQUALIZATION DEVICES AND METHODS, each of which parent application and provisional application is hereby incorporated by reference herein in its entirety.

FIELD

Illustrative embodiments of the disclosure generally relate to devices for separating body tissue such as adipose tissue in plastic surgical or other procedures. More particularly, illustrative embodiments of the disclosure relate to a tissue separation, equalization and regeneration devices and methods in which adipose or other tissue is separated, equalized, eradicated or regenerated without risking damage to blood vessels, nerves, skin or other structures in a plastic surgical or other procedure.

BACKGROUND

In plastic surgical procedures such as liposuction, it may be necessary to separate adjacent portions of adipose tissue from each other in the abdomen, face or other region of the body in which the procedure is carried out. Some types of fat reduction procedures may utilize eradication of adipose tissue from one or more regions of the body. One of the challenges of separating Or eradicating adipose tissue is that of effecting the separation or eradication without inadvertently incurring damage to blood vessels, nerves, skin or other structures.

Accordingly, fat separation, equalization and eradication devices and methods in which adipose or other tissue is separated, equalized or eradicated without risking damage to blood vessels, nerves, skin or other structures in a plastic surgical or other procedure are needed. Also desirable are devices and methods which can be used to regenerate ischemic or injured adipose tissue by inducing an "adipose injury cocktail" response in adipose-derived stromal cells (ASCs).

SUMMARY

The disclosure is generally directed methods of inducing apoptosis in a tissue. An illustrative embodiment of the methods includes providing a tissue separation and equalization device having a generally elongated tissue insertion member, providing an incision in tissue, inserting the tissue insertion member of the tissue separation and equalization device through the incision into the tissue, reducing a temperature of the tissue insertion member and removing the tissue insertion member from the tissue.

BRIEF DESCRIPTION OF THE DRAWINGS

Illustrative embodiments of the disclosure will, now be described, by way of example, with reference to the accompanying drawings, in which.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the claims. Moreover, the illustrative embodiments described herein are not exhaustive and embodiments or implementations other than those which are described heroin and which fall within the scope of the appended claims are possible. Furthermore, there is no intention to be bound by any expressed or implied theory presented in the preceding technical field, background, brief summary or the following detailed description.

Figure 1:
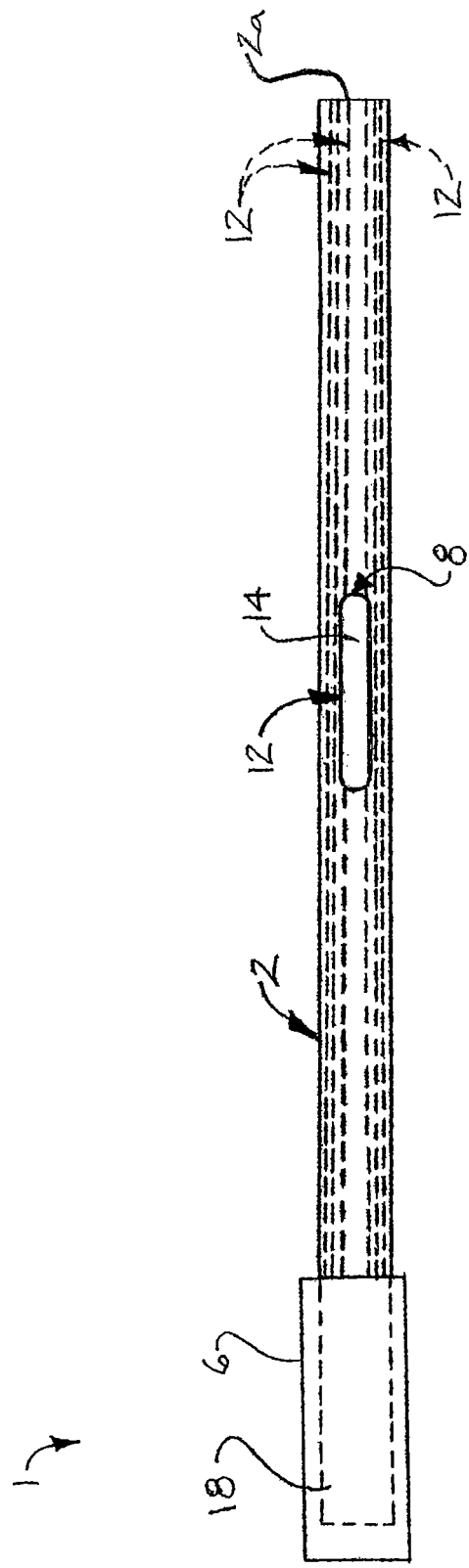
FIG. 1 is a side view of an illustrative embodiment of a tissue separation and equalization device.
Figure 2:
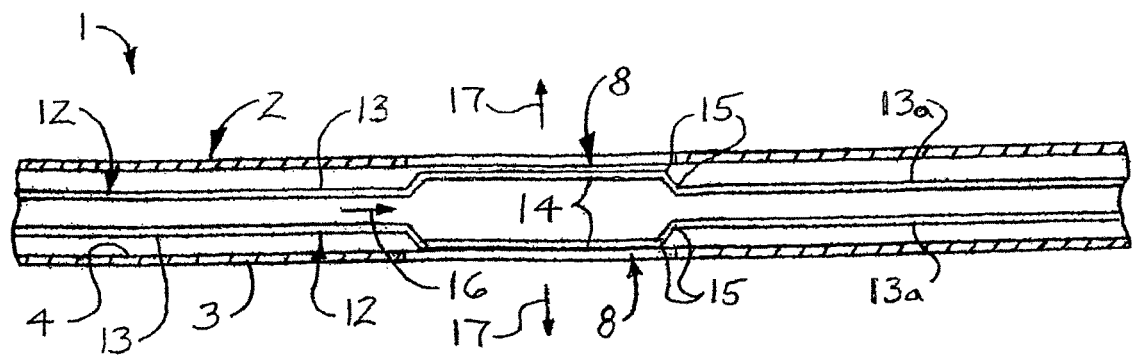
FIG. 2 is a longitudinal sectional view of an illustrative embodiment of the tissue separation and equalization device as illustrated in FIG. 1 with multiple tissue separating, members of the device deployed in a retracted configuration in a cannula of the device.

Referring initially to FIGS. 1-5 of the drawings, an illustrative embodiment of the fat separation and equalization device, hereinafter device, is generally indicated by reference numeral The device 1 includes a generally elongated tissue insertion member such as a cannula 2. As illustrated in FIG. 2, in some embodiments, the cannula 2 may have an elongated cannula wall 3 which encloses a cannula interior 4 and has a distal cannula end 2a. In other embodiments, the cannula 2 may have a substantially solid construction. The cannula 2 may be generally elongated and cylindrical and ma be a medical-grade plastic, metal or other material which is medically compatible and consistent with the functional requirements of the device 1. In some embodiments, the cannula 2 may have a diameter of about 2.5 mm or less. The cannula interior 4 of the cannula 2 may have a diameter of about 1.5 mm~2.0 mm or less.

Figure 4:
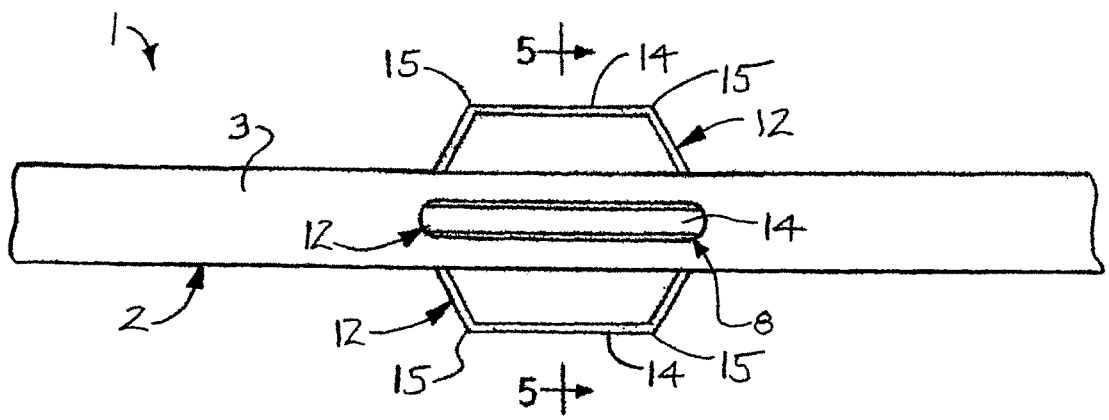
FIG. 4 is a side view, partially in section, of an illustrative embodiment of the tissue separation and equalization device as illustrated in FIG. 1, with the tissue separating members deployed in the expanded configuration.
Figure 5:
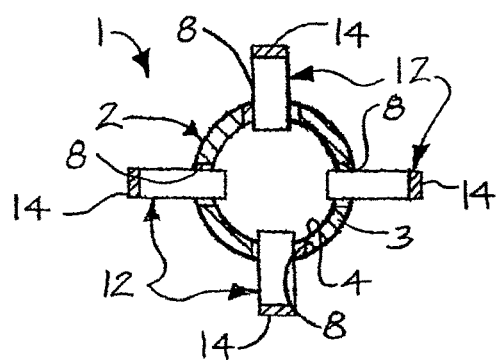
FIG. 5 is a cross-sectional view, taken along section lines 5-5 in FIG. 4.
Figure 6:
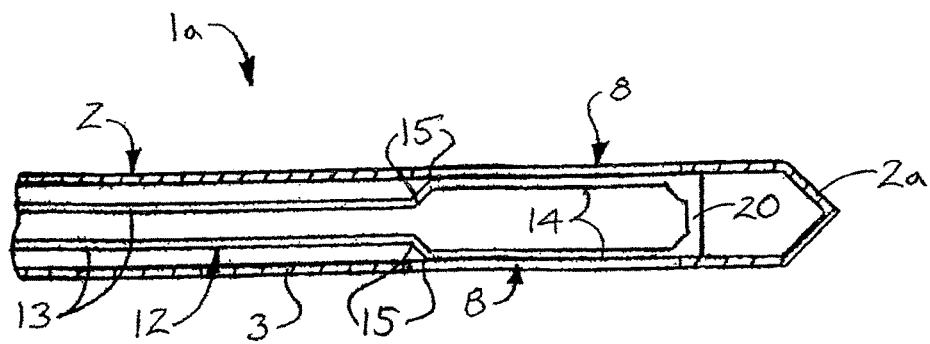
FIG. 6 is a longitudinal sectional view of an alternative illustrative embodiment of the tissue separation and equalization device, with the tissue separating members of the device deployed in a retracted configuration in a cannula.
Figure 7:
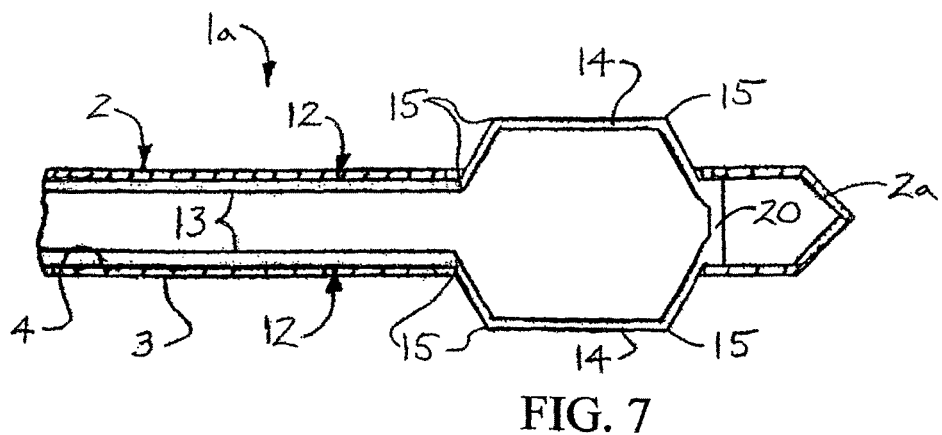
FIG. 7 is a longitudinal sectional view of an Illustrative embodiment of the tissue separation and equalization device as illustrated in FIG. 6, with the tissue separating members deployed in an expanded, tissue-separating configuration as they extend through respective tissue separating member openings in the cannula.
Figure 8:
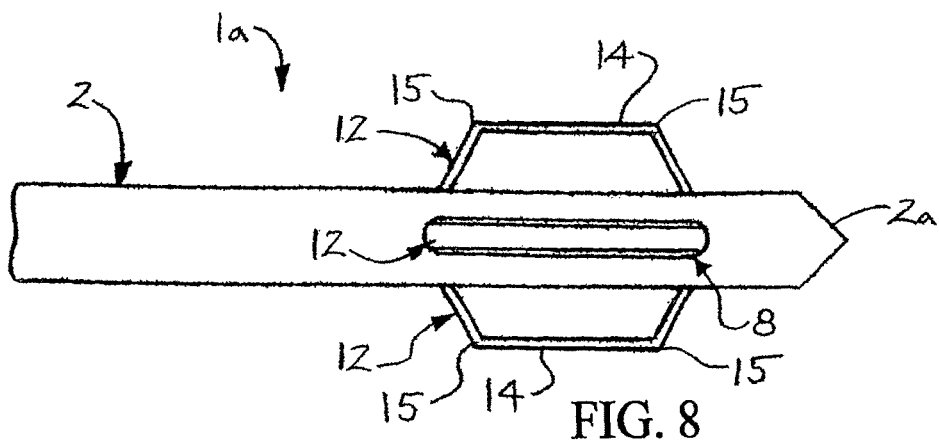
FIG. 8 is a side view of an illustrative embodiment of the tissue separation and equalization device as illustrated in FIG. 6 with the tissue separating members deployed in the expanded configuration.
Figure 9:
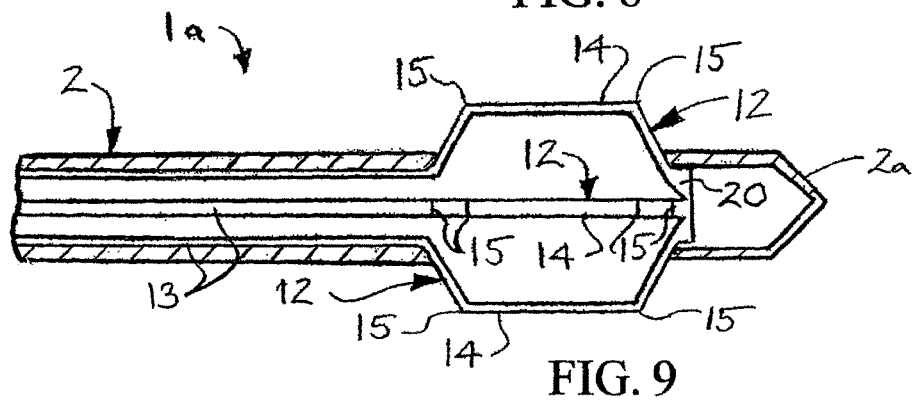
FIG. 9 is a longitudinal interior view of an illustrative embodiment of the device as illustrated in FIG. 6, with the cannula illustrated in longitudinal sectional view and the tissue separating members in non-section and deployed in the expanded configuration.

At least one member opening, hereinafter expansion member opening 8, may extend through the cannula wall 3 at selected locations along the length and the circumference of the cannula 2. As illustrated in FIGS. 1 and 4, each expansion member opening 8 may have a generally elongated, slotted shape. As illustrated in FIG. 5, in some embodiments of the device 1, four tissue separating member openings 8 may extend through the cannula wall 3 generally at 90 degrees with respect to each other around the circumference of the cannula wall 3. In other embodiments, a greater or lesser number of the tissue separating member openings 8 may extend through the cannula wall 3.

Figure 3:
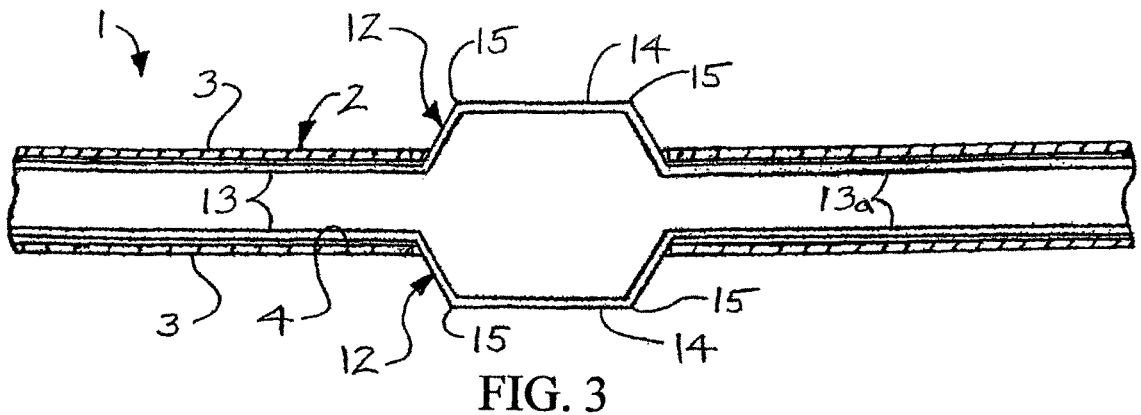
FIG. 3 is a longitudinal sectional view of an illustrative embodiment of the tissue separation and equalization device as illustrated in FIG. 1, with the tissue separating members deployed in an expanded, tissue-separating configuration as they protrude from respective tissue separating member openings in the cannula.

At least one expandable member, hereinafter tissue separating member 12, may extend longitudinally within the cannula interior 4 of the cannula 2. The tissue separating members 12 may correspond in number to the tissue separating member openings 8. In some embodiments, four tissue separating members 12 may be arranged around, the circumference of the cannula 2 at the positions of the respective tissue separating member openings 8. In other embodiments, the number of tissue separating members 12 may be greater or lesser than four. Each tissue separating member 12 may be an elongated rod or strip of flexible metal with an elongated proximal member segment 13, at least one expansion segment 14 extending from the proximal member segment 13 and a distal member segment 13a which extends from the expansion segment or segments 14 and may engage the distal cannula end 2a of the cannula 2. Bend lines 15 may he formed or shaped in the tissue separating member 12 to form or demarcate each expansion segment 14 from the proximal member segment 13 and the distal member segment 13a. The expansion segment or segments 14 of each tissue separating member 12 may generally register with a corresponding tissue separating member opening 8 in the cannula wall 3. Accordingly, upon shifting or displacement of the proximal member segment 13 of each tissue separating member 12 along the longitudinal axis of the cannula 2 in the cannula interior 4 toward the expansion segments 14, or in the direction indicated by the arrow 16 in FIG. 2, typically in a manner which will be hereinafter described, the distal member segment 13a remains stationary in the cannula interior 4, Consequently, the expansion segment 14 bends along the bend lines 15 and expands or buckles outwardly through the tissue separating member opening 8, as indicated by the arrows 17 in FIG. 2 and as illustrated in FIG. 3. Conversely, upon movement of the proximal member segment 13 of the tissue separating member 12 away from the expansion segment 14, or in the direction which is opposite the arrow 16, the expansion segment 14 straightens and is retracted back into the corresponding tissue separating member opening 8 as illustrated in FIG. 2. In embodiments in which the cannula 2 has a solid construction, each tissue separating member 12 may extend through a corresponding channel (not illustrated) in the cannula 2.

As illustrated in FIG. 1, the cannula 2 may be engaged by a cannula base 6. The cannula base 6 may be part of a hand piece (not illustrated) which can be grasped by an operator of the device 1 to facilitate deployment, expansion or outward buckling and retraction of the tissue separating members 12 relative to the tissue separating member openings 8. A driving mechanism 18 (illustrated in phantom) in the cannula base 6 may operably engage each tissue separating member 12 to facilitate bidirectional movement or longitudinal shifting or displacement of the proximal member segment 13 of the tissue separating member 12 within the cannula 2. The driving mechanism 18 may be any type of mechanism which is operable to engage and shift or displace the proximal member segments 13 of the tissue separating members 12 along an axis which is parallel to the longitudinal axis of the cannula 2, as indicated by the arrow 16 in FIG. 2. In some embodiments, the driving mechanism 8 may be a screw mechanism in which the tissue separating members 12 are shifted or displaced by mechanical actuation or rotation of a screw (not illustrated). In some embodiments, a locking device (not illustrated) may operably engage the tissue separating members 12 for the purpose of locking the tissue separating members 12 in the expanded, functionally-deployed position illustrated in FIGS. 3-5 according to the knowledge of those skilled in the art.

Figure 15:
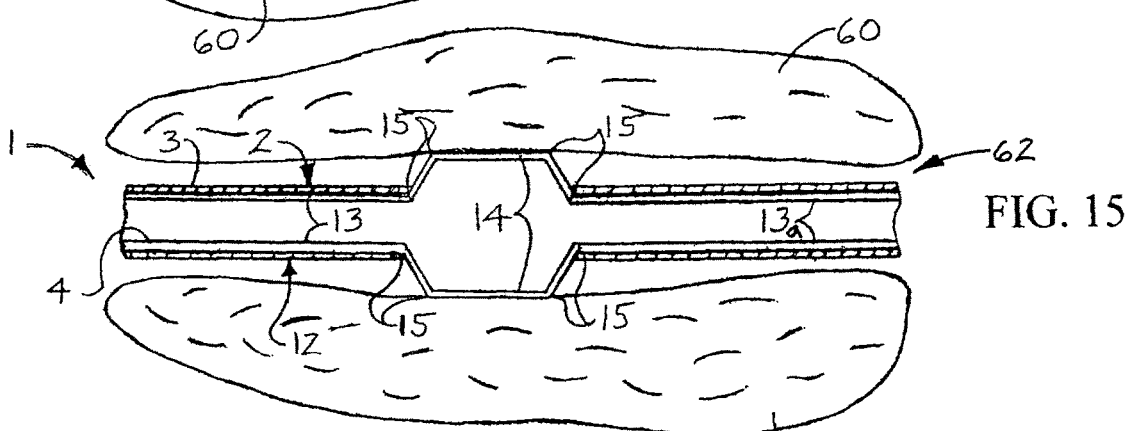
FIG. 15 is a longitudinal sectional view of an illustrative embodiment the tissue separation and equalization device as illustrated in FIG. 1, inserted between the adjacent portions of adipose tissue in separation of the adipose tissue portions, with the tissue separating members of the device deployed in the expanded configuration and extending from the respective tissue separating member openings in the cannula and separating the adjacent portions of adipose tissue from each other.
Figure 16:
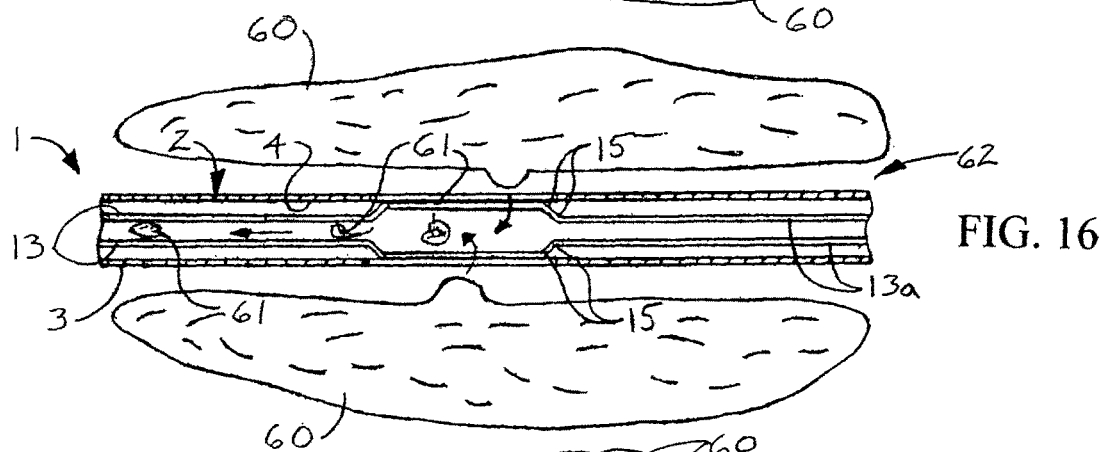
FIG. 16 is a longitudinal sectional view of an illustrative embodiment of the tissue separation and equalization device as illustrated in FIG. 1, with the tissue separating members of the device deployed in the retracted configuration in the cannula after separation of the adipose tissue portions, more particularly illustrating aspiration of adipose tissue after separation of the adipose tissue portions.
Figure 17:
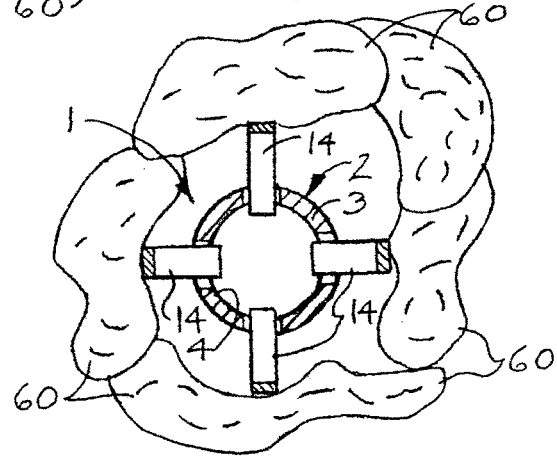
FIG. 17 is a cross-sectional view of an illustrative embodiment of the tissue separation and equalization device as illustrated in FIG. 1, with the tissue separating members of the device deployed in the expanded configuration and separating the adjacent portions of adipose tissue from each other.

Referring next to FIGS. 14-17 of the drawings, in exemplary application, the device 1 is used to separate adjacent portions of adipose tissue 60 from each other in a liposuction or other plastic surgical, or other procedure. Accordingly, a small incision (not illustrated) is made in the skin of the patient and the cannula 2 is inserted through the incision into the adipose tissue. The driving mechanism 18 (FIG. 1) is operated to shift or displace the proximal member segment 13 of each tissue separating member 12 in the cannula 2 in the direction toward the initially stationary expansion segments 14, as indicated by the arrow 16 in FIG. 2, while the distal member segment 13a remains stationary, This action causes the expansion segments 14 of the respective tissue separating members 12 to buckle or expand from the respective tissue separating member openings 8 and engage and separate the portions of adipose tissue 60 from each other, as illustrated in FIGS. 15 and 17, forming a tissue space 62 between the separated portions of adipose tissue 60. In subsequent steps, the driving mechanism 18 (FIG. 1) may be operated to release and return the tissue separating members 12 to the retracted position as illustrated in FIG. 16 as the expansion segments 14 typically recoil from the expanded position to the retracted position. Finally, the cannula 2 is withdrawn from the tissue space 62 and the incision.

As illustrated in FIG. 16, in some embodiments of the device 1, suction device (not illustrated), which may be conventional, may be provided in fluid communication with the cannula interior 4. Therefore, after the adipose tissue 60 is separated as illustrated in FIG. 15 and the tissue separating members 12 are retracted back into the tissue separating member openings 8, as illustrated in FIG. 16, the suction device may be operated to draw a vacuum on the cannula interior 4 and aspirate adipose tissue pieces 61 through the tissue separating member openings 8 and/or other opening (not illustrated) in the cannula 2 and the cannula interior 4 into the suction device. In some embodiments, the suction device may be attachable to the cannula 2 at the same point and using the same mechanism of attachment of the cannula base 6 to the cannula 2, in which case the cannula base 6 is first detached from the cannula 2 before attachment of the suction device to the cannula 2. Alternatively, the suction device may be attached to the cannula 2 through a dedicated port (not illustrated) which communicates with the cannula interior 4 of the cannula 2.

Referring next to FIGS. 6-9 of the drawings, another illustrative embodiment of the tissue separation and equalization device is generally indicated by reference numeral 1a. The tissue separating member openings 8 of the device 1a a may be disposed generally adjacent to a distal cannula end 2a of the cannula 2. In some embodiments, the distal cannula end 2a may be tapered or sharpened, as illustrated. The tissue separating members 12 may terminate on a connecting portion 20 which may be provided, in the cannula interior 4 between the tissue separating member openings 8 and the distal cannula end 2a. Accordingly, upon operation of the device 1a, longitudinal shifting or displacement of the member segments 13 of the tissue separating members 12 toward the tissue separating member openings 8 and the stationary connecting portion 20 causes the expansion segments 14 to expand or buckle outwardly through the respective tissue separating member openings 8 in the cannula 2. Operation of the device 1a may be as was heretofore described with respect to operation of the device 1 in FIGS. I -5.

Figure 10:
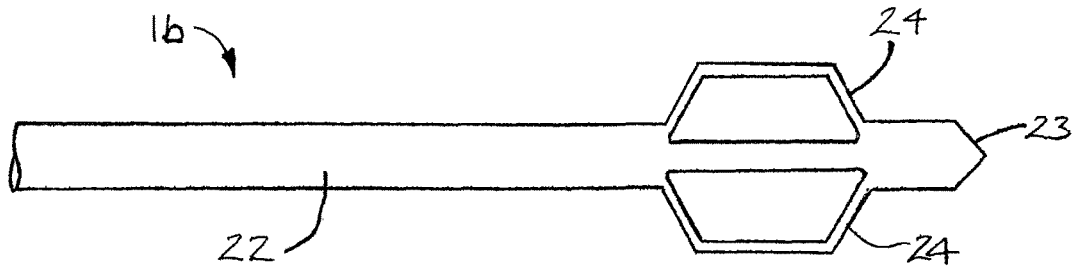
FIG. 10 is a side view, partially in section, of another illustrative embodiment of the tissue separation and equalization device.

Referring next to FIGS. 10 of the drawings, another illustrative embodiment of the tissue separation and equalization device is generally indicated by reference numeral 1b. The device 1b may include a generally elongated tissue insertion member such as a device shaft 22 which may be solid in construction and has a distal shaft end 23, In some embodiments, the distal shaft end 23 may have a tapered or sharpened configuration, as illustrated. In some embodiments, the device shaft 22 may have a diameter of about 2.5 mm or less. At least one expanded member, hereinafter tissue separating member 24, extends outwardly from and in fixed relationship to the device shaft 22. In some embodiments, the tissue separating member or members 24 may be disposed generally adjacent to the distal shaft end 23 of the device shaft 22. The tissue separating members 24 may be fixed in an expanded position with respect to the device shaft 22. In sonic embodiments, four tissue separating members 24 may extend outwardly from the device shaft 22 at generally a 90-degree angle with respect to each other around the circumference of the device shaft 22. In other embodiments, a greater or lesser number of the tissue separating members 24 may extend from the device shall 22. In exemplary, use, the device 1b is inserted through an incision (not illustrated) in the skin of a patient. The tissue separating members 24 separate adjacent portions of adipose tissue from each other as the device 1b is slid into the tissue through an incision into the tissue in a liposuction or other surgical procedure.

Figure 11:
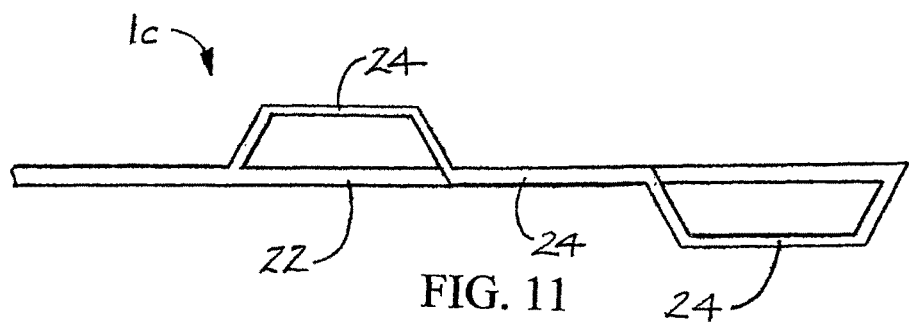
FIG. 11 is a side view, partially in section, of still another illustrative embodiment of the tissue separation and equalization device.

Referring next to FIG. 11 of the drawings, another illustrative embodiment of the tissue separation and equalization device is generally indicated by reference numeral 1c, The device 1c may include multiple tissue separating members 24 which extend from the device shaft 22 in adjacent relationship to each other along the longitudinal axis of the device shaft 22. Adjacent tissue separating members 24 may he oriented at an angle with respect to each other about the circumference of the device shaft 22. In some embodiments, adjacent tissue separating members 24 may be oriented at generally a 45-degree angle with respect to each other around the circumference of the device shaft 22. In other embodiments, adjacent tissue separating members 24 may be oriented at generally a 90-degree or other angle with respect to each other around the circumference of the device shaft 22. In some embodiments, the tissue separating members 24 may be arranged along the longitudinal axis of the device shaft 22 at a spacing of about 1~2 cm, Use of the tissue separation and equalization device 1c may be as was heretofore described, with respect to the device 1b in FIG. 10.

Figure 12:
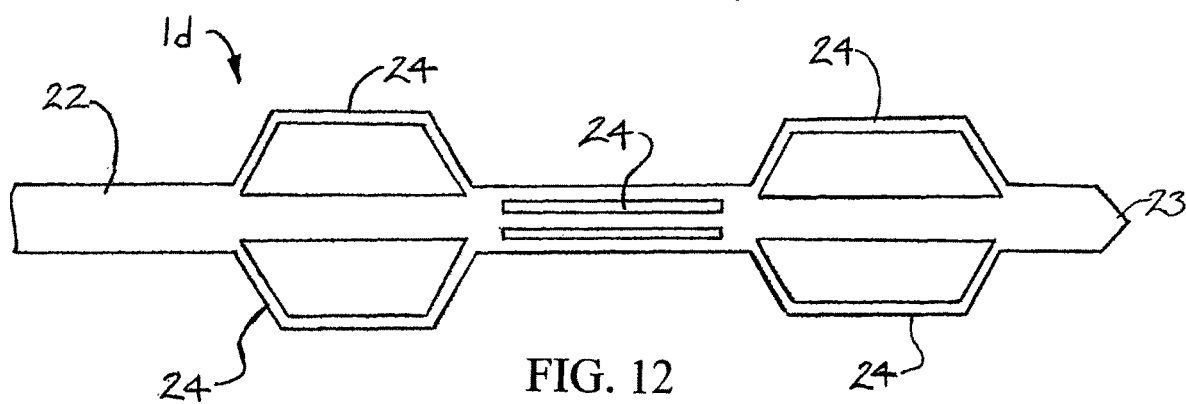
FIG. 12 is a side view, partially in section, of yet another illustrative embodiment of the tissue separation and equalization device.

Referring next to FIG. 12 of the drawings, another illustrative embodiment of the tissue separation and equalization device is generally indicated by reference numeral 1d. The device 1d may include multiple pairs of adjacent tissue separating members 24 which extend outwardly from opposite sides of the device shaft 22 at a generally 180-degree angle with respect to each other. Adjacent pairs of tissue separating members 24 along the longitudinal axis of the device shaft 22 may be oriented at a generally 90-degree angle with respect to each other around the circumference of the device shaft 22. Accordingly, the 180-degree separated pairs of tissue separating members 24 may alternate between the two orientations toward the distal shaft end 23 of the device shaft 22. The device 1d may be particularly suitable for repeat liposuction procedures in which the adipose tissue offers increased resistance to passage of the device 1d through the tissue. Use of the tissue separation and equalization device Id may be as was heretofore described with respect to the device 1b in FIG. 10.

Figure 13:
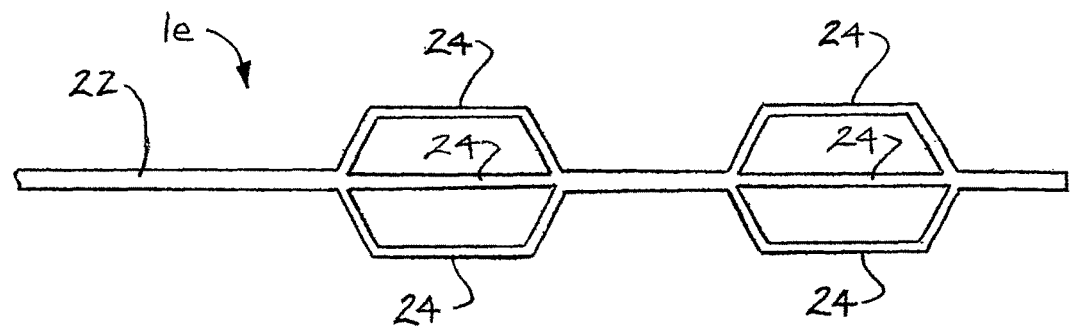
FIG. 13 is a side view, partially in section, of another illustrative embodiment of the tissue separation and equalization device.
Figure 14:
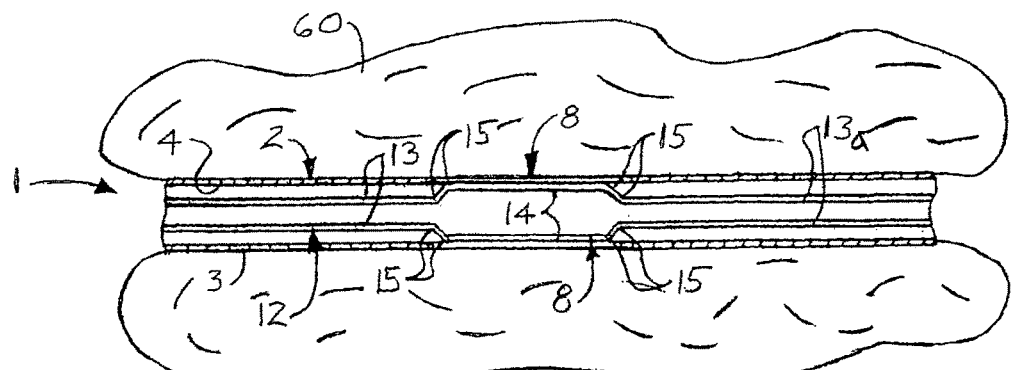
FIG. 14 is a longitudinal sectional view of an illustrative embodiment of the tissue separation and equalization device as illustrated in FIG. 1, inserted between adjacent portions of adipose tissue preparatory to separation of adjacent adipose tissue portions, with the tissue separating members of the device initially deployed in the retracted configuration in the cannula.

Referring next to FIG. 13 of the drawings, another illustrative embodiment of the tissue separation and equalization device is generally indicated by reference numeral 1e. The device 1e may include multiple adjacent sets of multiple tissue separating members 24 which extend outwardly from and along the longitudinal axis of the device shaft 22. Each set may include four tissue separating members 24 which extend outwardly from the device shaft 22 at a generally 90-degree angle with respect to each other around the circumference of the device shaft 22. The device le may be particularly suitable for separating adipose tissue in micro cannula design liposuction applications in areas such as the face and other areas of tight skin. Use of the tissue separation and equalization device 1e may be as was heretofore described with respect to the device 1b in FIG. 10.

It will be appreciated by those skilled in the art that the various embodiments of the tissue, separation and equalization device described herein significantly expedite separation of adipose tissue in liposuction or other surgical procedures by up to an estimated five-fold.

Figure 18:
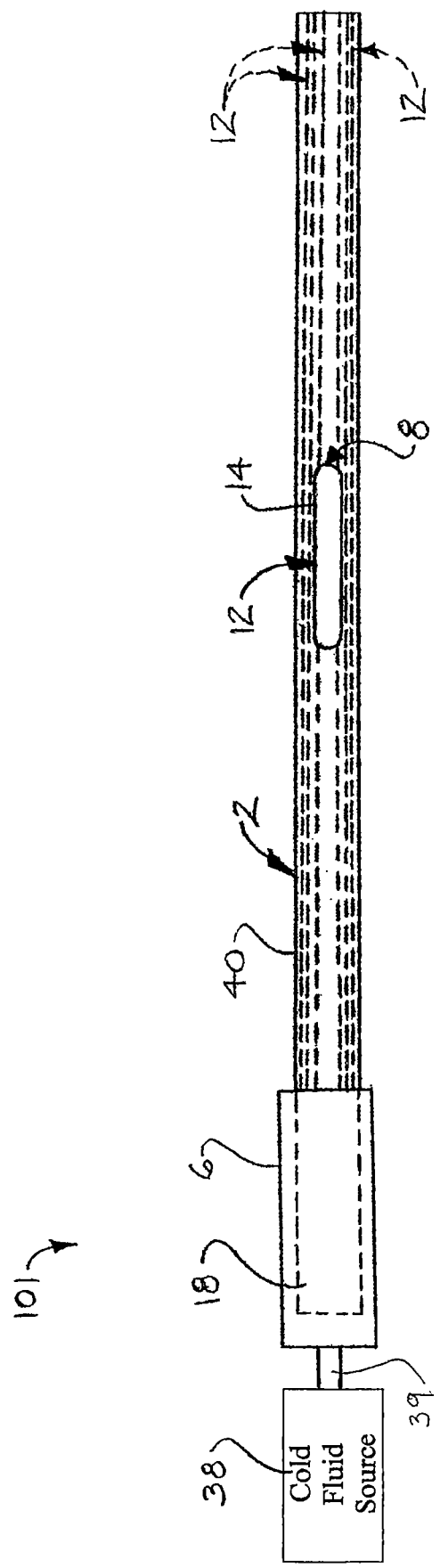
FIG. 18 is a partially schematic side view of an illustrative embodiment of an adipose tissue separation, equalization and eradication device.

Referring next to FIGS. 18-22 of the drawings, an illustrative embodiment of an adipose tissue separation, equalization and eradication device, hereinafter device, is generally indicated by reference numeral 101. The device 101 may have a design which is similar to that of the tissue separation and equalization device which was heretofore described with respect to FIGS. 15, where like reference numerals designate like elements. A temperature reducine fluid source, hereinafter cold fluid source 38, which is a source of temperature reducing fluid, hereinafter cold fluid 41, is disposed in fluid communication with the cannula interior 4 (FIG. 19) of the cannula 2 of the device 101. The cold fluid source 38 may be a source of cold saline solution, for example and without limitation, or any other pharmacologically-safe fluid which is suitable for the purpose. In exemplary applications, the cold fluid source 38 may be a source of cold fluid having a temperature of from about −21.12° C. to about 0° C. The cold fluid source 38 may include a pump and supply mechanism which is adapted to pump the cold fluid 41 (FIG. 21) through the cannula interior 4 of the Bann ala 2 according to the knowledge of those skilled in the art. In some embodiments, the cold fluid source 38 may he disposed in fluid communication with the cannula interior 4 of the cannula 2 through the cannula base 6, such as via a cold fluid conduit 39, as illustrated in FIG. 18. In other embodiments, the cold fluid source 38 may he attachable to the cannula 2 at the same point and using the same mechanism of attachment of the cannula base 6 to the cannula 2, in which case the cannula base 6 may first be detached from the cannula 2 before attachment of the cold fluid source 38. In still other embodiments, the cold fluid source 38 may be attached to the cannula 2 through a dedicated port (not illustrated) which communicates with the cannula interior 4 of the cannula 2. A thermally-insulated lining 40 which includes a thermally-insulating material may coat the exterior surface of the cannula 2.

Figure 19:
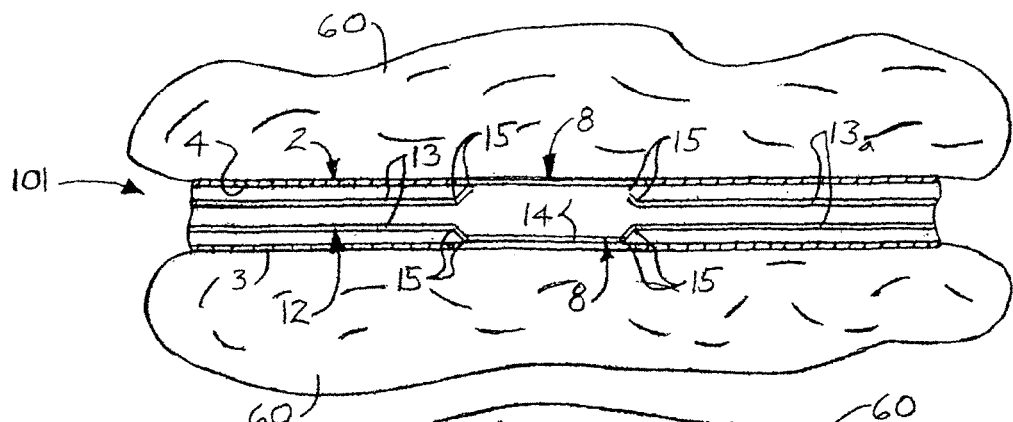
FIG. 19 is a longitudinal sectional view of an illustrative embodiment of the tissue separation, equalization and eradication device as illustrated in FIG. 18, inserted between adjacent portions of adipose tissue preparatory to separation of the adipose tissue portions, with the tissue separating members of the device initially deployed in the retracted configuration in the cannula.
Figure 20:
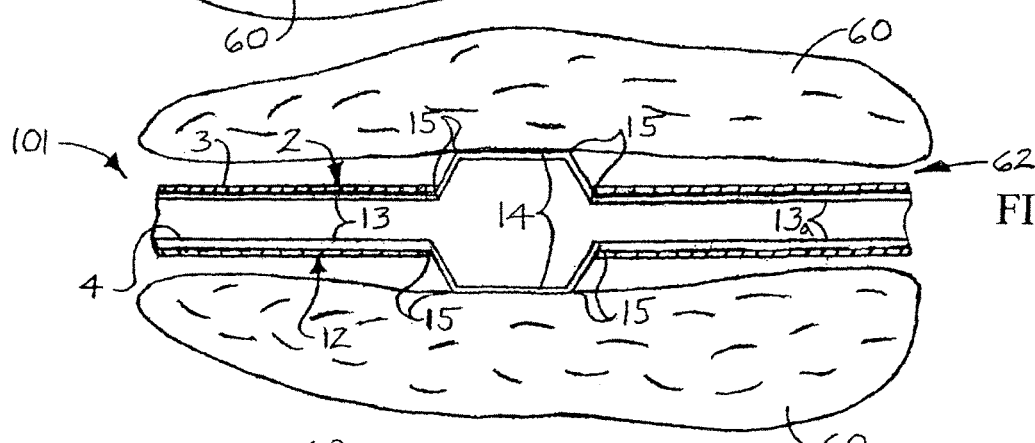
FIG. 20 is a longitudinal sectional view of an illustrative embodiment of the tissue separation, equalization and eradication device as illustrated in FIG. 18, inserted between adjacent portions of adipose tissue, with the tissue separating members of the device deployed in an expanded configuration and extending from the respective tissue separating member openings in the cannula and separating to adjacent portions of adipose tissue from each other.
Figure 21:
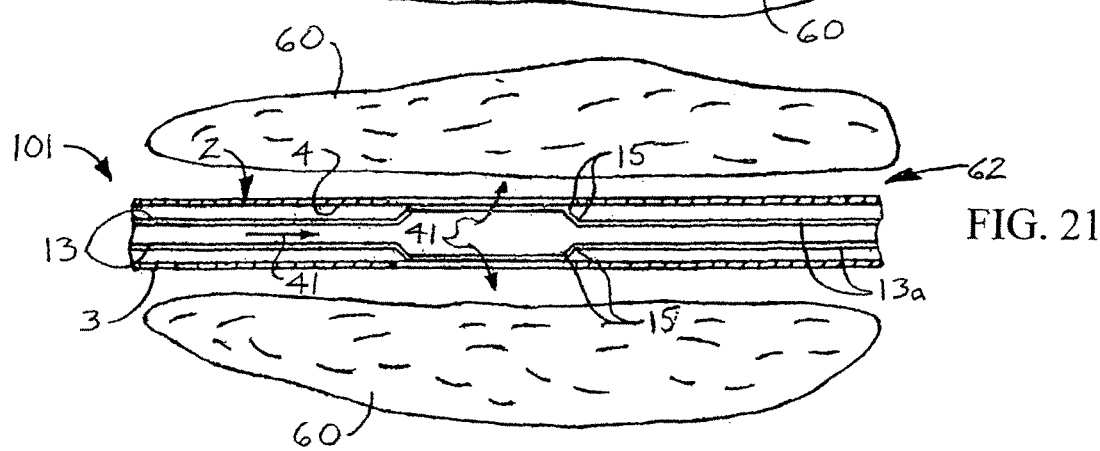
FIG. 21 is a longitudinal sectional view of an illustrative embodiment of the tissue separation, equalization and eradication device as illustrated in FIG. 18, with the tissue separating members of the device deployed in the retracted configuration in the cannula, more particularly illustrating introduction of a cold fluid from the device into a tissue space in the adipose tissue after separation of the tissue.

As illustrated in FIGS. 19-22, in exemplary application, the device 101 may he used to initially separate adipose tissue 60 in a patient as was heretofore described with respect to the device 1 in FIGS. 14-17 and as illustrated in FIGS. 19 and 20. After separation of the portions of adipose tissue 60 is effected, a supply of the cold fluid 41 is pumped from the cold fluid source 38 (FIG. 18) through the cannula interior 4. In some embodiments, the cold fluid 41 may flow from the cannula interior 4 through the tissue separating member openings 8 into the tissue space 62 between the portions of the adipose tissue 60. In other embodiments, fluid dispensing openings (not illustrated) may be provided in the cannula wall 3 along the length of the cannula 2 to dispense the cold fluid 41 from the cannula interior 4 through the fluid dispensing openings and into the tissue space 62.

Figure 22:
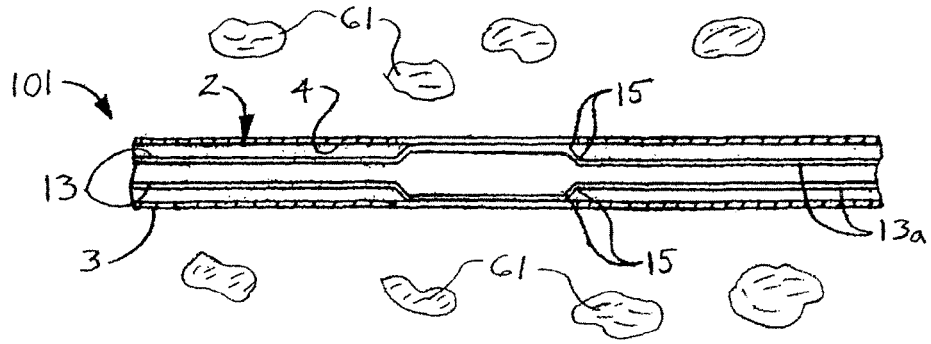
FIG. 22 illustrates a section of adipose tissue after eradication treatment of the adipose tissue with the cold fluid using the device in FIG. 21.

As illustrated its FIG. 22, the cold fluid 41 which is dispensed from the cannula interior 4 into the tissue space 62 contacts and induces apoptosis in the adipose tissue 60. Consequently most or a significant portion of the adipose tissue 60 is eradicated from the area in which the cold fluid 41 is dispensed. The eradication treatment may be repeated in adjacent areas of the tissue, as deemed necessary, to reduce the adipose tissue content of the area or areas of the patient in which the treatment is carried out.

It will be recognized and understood that while the description of the tissue separation, equalization and eradication, device 101 in FIGS. 18-22 is based on the design of the tissue separation and equalization device 1 of FIGS. 2-5, the eradication treatment capability is equally adaptable to the designs of the tissue separation and equalization device 1a which was heretofore described with respect to FIGS. 6-9 and the tissue separation and equalization devices 1b-1e which were heretofore described with respect to FIGS. 10-13, respectively.

Figure 23:
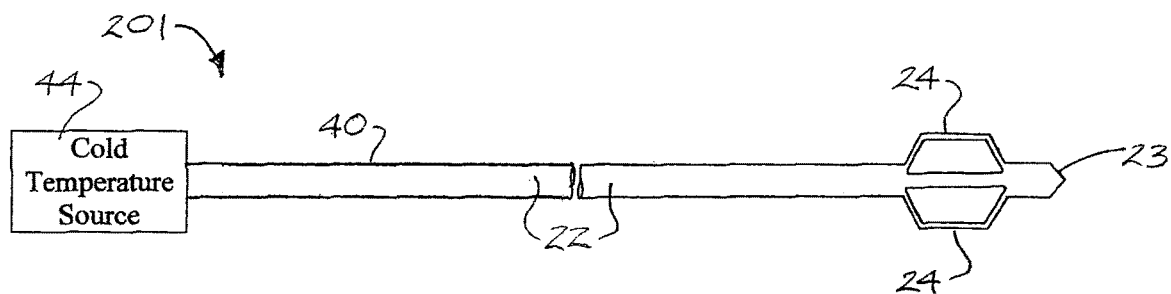
FIG. 23 is a partially schematic side view, partially in section, of an alternative illustrative embodiment of an adipose tissue separation, equalization arid eradication device.
Figure 24:
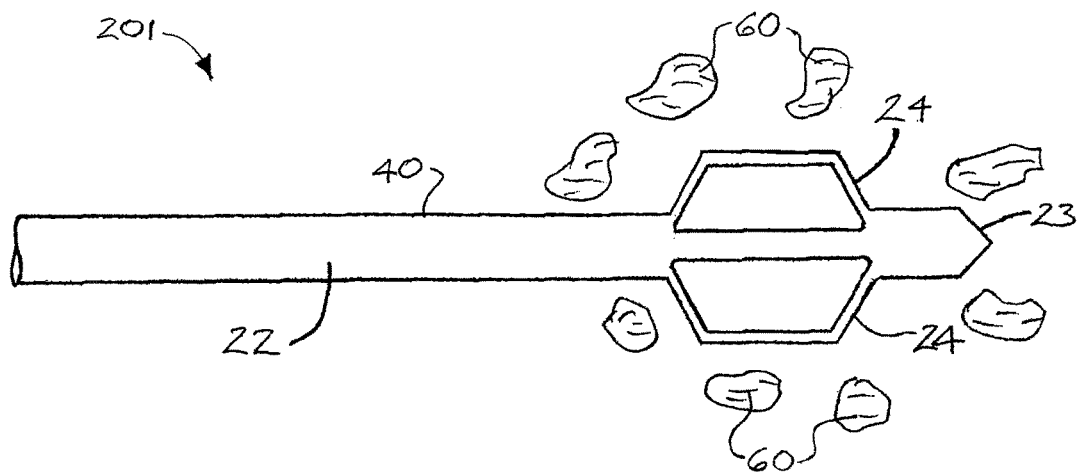
FIG. 24 is a side view, partially in section, of an adipose tissue separation, equalization and eradication device as illustrated in FIG. 23, after eradication treatment of the adipose tissue using the device.

Referring next to FIGS. 23 and 24 of the drawings, an alternative illustrative embodiment of an adipose tissue separation, equalization and eradication device, hereinafter device, is generally indicated by reference numeral 201. The device 201 may have a design which is similar to that of the device 1b that was heretofore described with respect to FIG. 10, where like reference numerals designate like elements. The device shaft 22 and the tissue separating members 24 may be stainless steel or other medical-grade thermally-conductive metal or material which is suitable for surgical applications.

A cold temperature source 44 is disposed in thermal contact with the device shaft 22 to reduce the temperature of the device shaft 22 to a desired target temperature or temperature range. In exemplary applications, the cold temperature source 44 may be adapted to reduce the temperature of the device shaft 22 to a target temperature of from about −21.12° C. to about 0° C. The cold temperature source 44 may be any source of cold temperature which is known by those skilled in the art and suitable for the functional requirements of the device 201. For example and without limitation, in some embodiments, the cold temperature source 44 may utilize a source of refrigerant (not illustrated) to maintain the device shaft 22 at a reduced temperature via compression and evaporation of the refrigerant according to conventional methods known by those skilled in the art. A thermally-insulated lining 40 may coat the portion of the device shaft 22 which is adjacent to the cold temperature source 44.

As illustrated in FIG. 24, in exemplary application, the device 201 may he used to initially separate adipose tissue 60 by insertion of the device 201 into adipose tissue in a patient, as was heretofore described with respect to the device 1b in FIG. 10. After separation of the portions of adipose tissue 60 is effected, the cold temperature source 44 may be operated to reduce the temperature of the device shaft 22 by thermal conduction to the, desired target temperature or temperature range. The reduced-temperature tissue separatmg members 24, distal shaft end 23 and device shaft 22 contact and induce apoptosis in the adipose tissue 60. Consequently, most or a significant portion of the adipose tissue 60 is eradicated from the area in which the device 201 is inserted. The eradication treatment may be repeated in adjacent areas of the tissue, as deemed necessary, to reduce the adipose tissue content of the area or areas of the patient in which the treatment is carried out.

It will he recognized and understood that while the description of the tissue separation, equalization and eradication device 201 in FIGS. 23 and 24 is based on the design of the tissue separation and equalization device 1b of FIG. 10, the eradication treatment capability is equally adaptable to the designs of the tissue separation and equalization devices 1c-1e which were heretofore described with respect to FIGS. 10-13, respectively. Moreover, the eradication treatment capability may also be adapted to the designs of the tissue separation and equalization device 1 heretofore described with respect to FIGS. 1-5 and the tissue separation and equalization device 1a heretofore described with respect to FIGS. 6-9.

Figure 25:
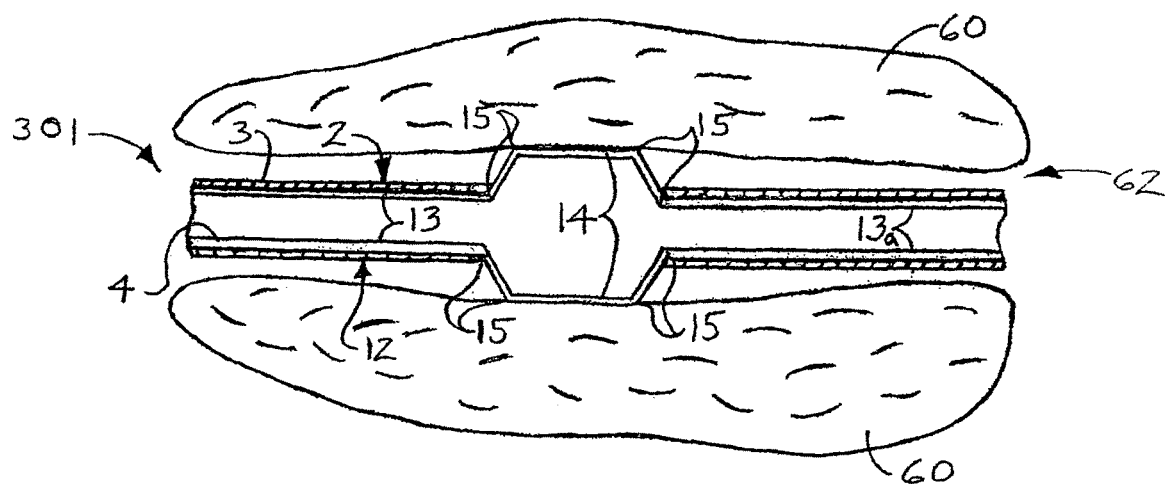
FIG. 25 is a longitudinal sectional view of an illustrative embodiment of a tissue separation, equalization and regeneration device, inserted between adjacent portions of adipose tissue in separation of the adipose tissue portions preparatory to regeneration treatment of the adipose tissue.
Figure 26:
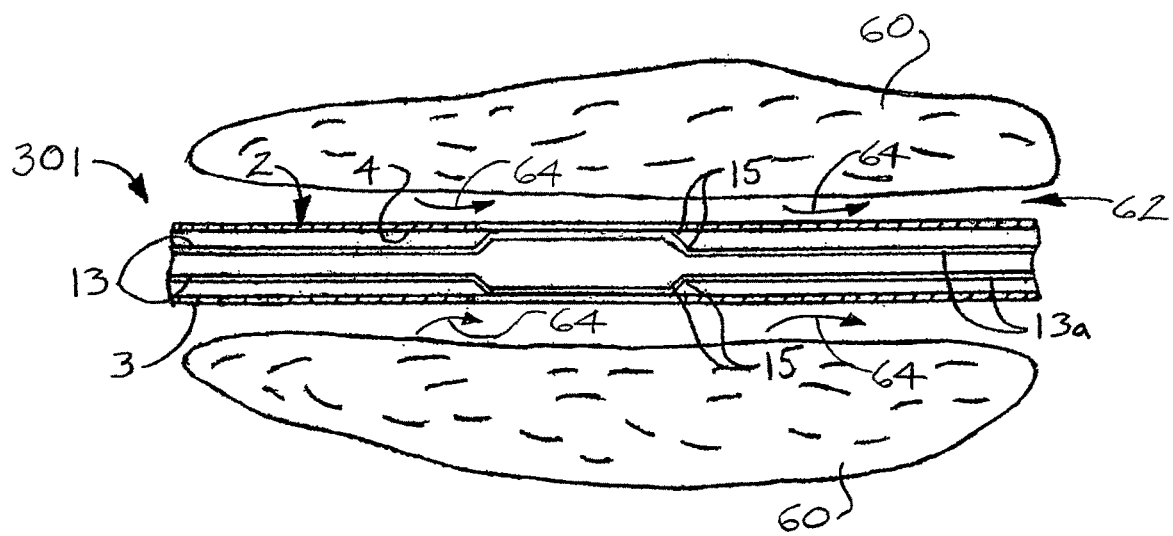
FIG. 26 is a longitudinal sectional view of an illustrative tissue separation, equalization and regeneration device as illustrated in FIG. 25, with the tissue separating members of the device deployed in the retracted configuration in the cannula and more particularly illustrating stimulation of an "adipose injury cocktail" in the adipose tissue responsive to separation of adipose tissue portions.
Figure 27:
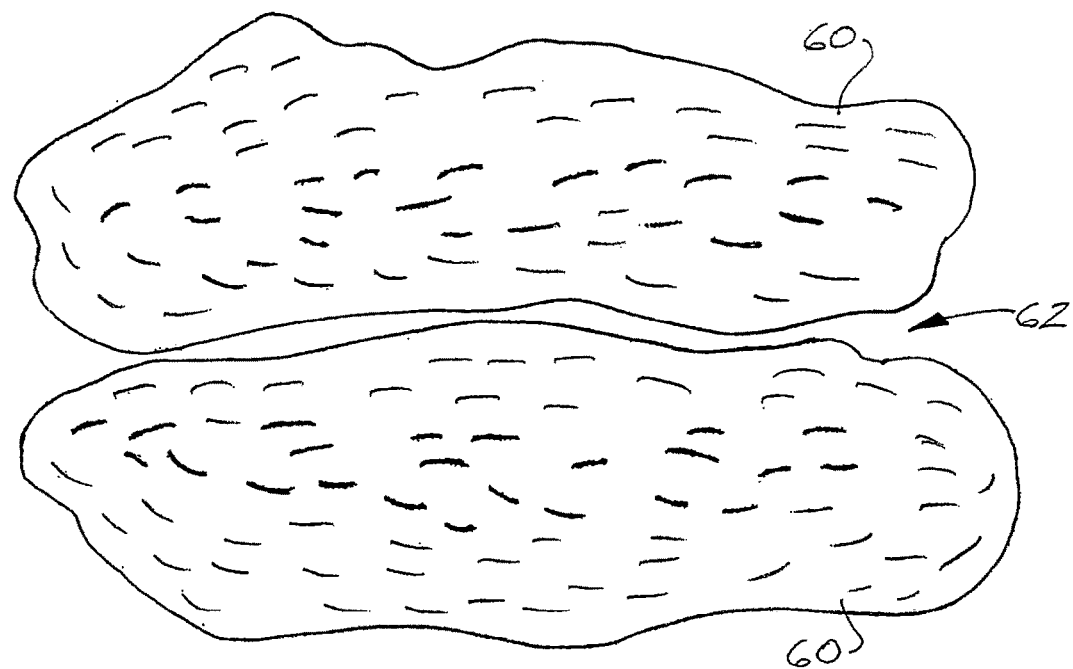
FIG. 27 illustrates regenerated adipose tissue responsive to regeneration treatment of the adipose tissue using the device as illustrated in FIGS. 25 and 26.

Referring next to FIGS. 25-27 of the drawings, an illustrative embodiment of a tissue separation, equalization and regeneration device 301, hereinafter device 301, which facilitates regeneration treatment of adipose tissue 60 is illustrated. The device 301 is adapted to facilitate regeneration of ischemic or injured adipose tissue 60 by inducing apoptosis in the adipose tissue 60, eliciting an "adipose injury cocktail" response in adipose-derived stromal cells (ASCs) in the adipose tissue 60. The device 301 may have a design which is the same as or similar to that of the device 1 heretofore described with, respect to FIGS. 14, where like reference numerals designate like elements in FIGS. 25 and 26.

In a process known as "compensatory proliferation", apoptotic cells release signals which activate stem/progenitor cells to divide and replace the apoptotic cell. Upon activation of adipose-derived stromal cells (ASCs) after injury of the cells, critical soluble factors are released from the apoptotic adipose cells and/or the extracellular matrix. The released factors mediate the compensatory proliferation of ASCs and recruitment of bone marrow-derived progenitor stem cells, leading to subsequent repair of the tissue.

It has been found that clinical injury to adipose tissue causes a number of soluble factors to be sequentially released at the injured site. These soluble factors include bFGF, PDGF, EGF and TGF-β, which are released in the early (coagulation) phase (day 0-1) of wound healing. Other factors which include VEGF, HGF, IL-8 and matrix metalloproteinase-1 gradually increase up to the late proliferation phase (day 5-7). Additional factors including KGF. IL-6 and matrix metalloproteinase-8 peak during the inflammatory phase (day 2-4). These growth factors function as an "adipose injury cocktail" which promote angiogenesis and improve oxygen tension in ischemic or diabetic adipose tissue by activating resident ASCs. The process is set forth more fully in "in vivo manipulation of stern cells for adipose tissue repair/reconstruction", *Regen. Med.* (2011) 6 (6 Suppl.), 33-4, which is hereby incorporated by reference herein in its entirety.

In exemplary application, the device 301 is used to stimulate the release of soluble factors 64 (FIG. 26) which regenerate adipose tissue 60 by promoting angiogenesis and adipose cell, proliferation in the adipose tissue 60. Accordingly, the cannula 2 is inserted into adipose tissue 60 in a patient typically through an incision (not illustrated) in the patient's skin, as was heretofore described. The driving mechanism 18 (FIG. 1) is operated to expand the expansion segments 14 of the tissue separating members 12 through the respective tissue separating member openings 8 in the cannula such that the expansion segments 14 engage and separate the portions of adipose tissue 60 from each other, as illustrated in FIG. 26, forming a tissue space 62 between the separated portions of adipose tissue 60. In subsequent steps, the driving mechanism 18 (FIG. 1) may be operated to release and return the tissue separating members 12 to the retracted position as illustrated in FIG. 26 and the cannula 2 withdrawn from the tissue space 62 and the incision. As further illustrated in FIG. 26, the trauma to the adipose tissue 60 which results upon separation of the adipose tissue 60 by operation of the device 301 induces the adipose tissue 60 to release the soluble factors 64, which promote angiogenesis and adipose cell proliferation in the adipose tissue 60 to regenerate the adipose tissue 60, as illustrated, in FIG. 27.

The foregoing regeneration procedure may he repeated in adjacent areas to regenerate the adipose tissue by facilitating angiogenesis and adipose cell proliferation in the tissue. It will he recognized and understood that the adipose tissue regeneration process may be carried out using the tissue separation and equalization devices 1 and 1a-1e, described herein above, in a similar manner.

Figure 28:
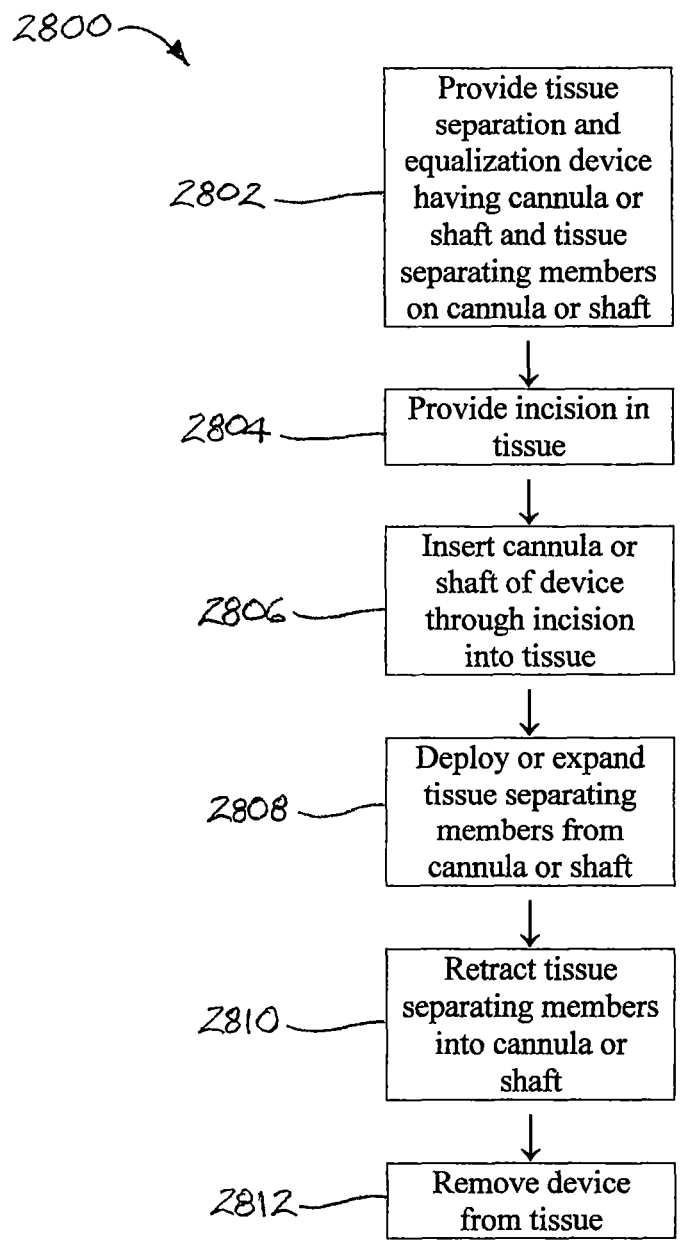
FIG. 28 is a flow diagram of an illustrative embodiment of a tissue separation and equalization method.

Referring next to FIG. 28, a flow diagram 2800 of an illustrative embodiment of a tissue separation and equalization method is illustrated. In block 2802, a tissue separation and equalization device having a tissue insertion member such as a cannula or shaft and tissue separating members on the cannula or shaft is provided. In some embodiments, the tissue separating members may be selectively expandable from respective openings in the cannula or shaft. In other embodiments, the tissue separating members may he fixed in an expanded configuration on the cannula or shaft. In block 2804, an incision is made in a tissue. In block 2806, the cannula or shaft of the device is inserted through the incision. In block 2808, the tissue separating members may he expanded or deployed from respective openings in the cannula shaft The tissue separating members separate adipose tissue portions and define a tissue space between the adipose tissue portions. In block 2810, the tissue separating members may be retracted into the cannula or shaft in some embodiments. In block 2812, the device is removed from the tissue.

Figure 29:
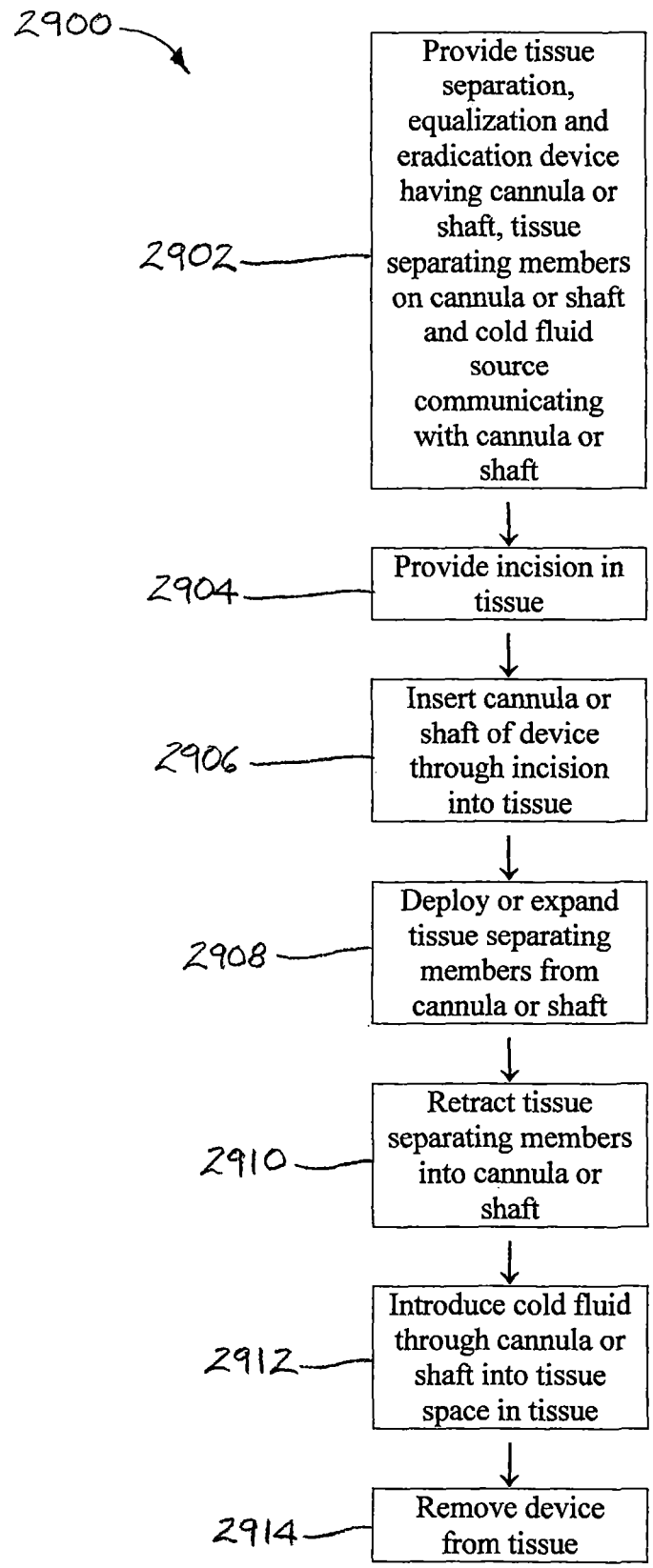
FIG. 29 is a flow diagram of an illustrative embodiment of a tissue separation, equalization and eradication method.

Referring next to FIG. 29, a flow diagram 2900 of an illustrative embodiment of a tissue separation, equalization and eradication method is illustrated. In block 2902, a tissue separation, equalization and eradication device is provided. The device has a tissue insertion member such as a cannula or shaft, tissue separating members, on the cannula or shaft arid a cold fluid source communicating with the cannula or shaft. In some embodiments, the tissue separating members may be selectively expandable from respective openings in the cannula or shaft. In other embodiments, the tissue separating members may he fixed in an expanded configuration on the cannula or shaft. In block 2904, an incision is made in a tissue. In block 2906, the cannula or shalt of the device is inserted through the incision. In block 2908, the tissue separating members may be expanded or deployed from respective openings in the cannula or shaft. The tissue separating members separate adipose tissue portions and define a tissue space between'the adipose tissue portions. In block 2910, the tissue separating members may be retracted into the cannula or shaft in some embodiments. In block 2912, cold fluid is introduced through the cannula or shaft into the tissue space. In block 2914, the device is removed from the tissue.

Figure 30:
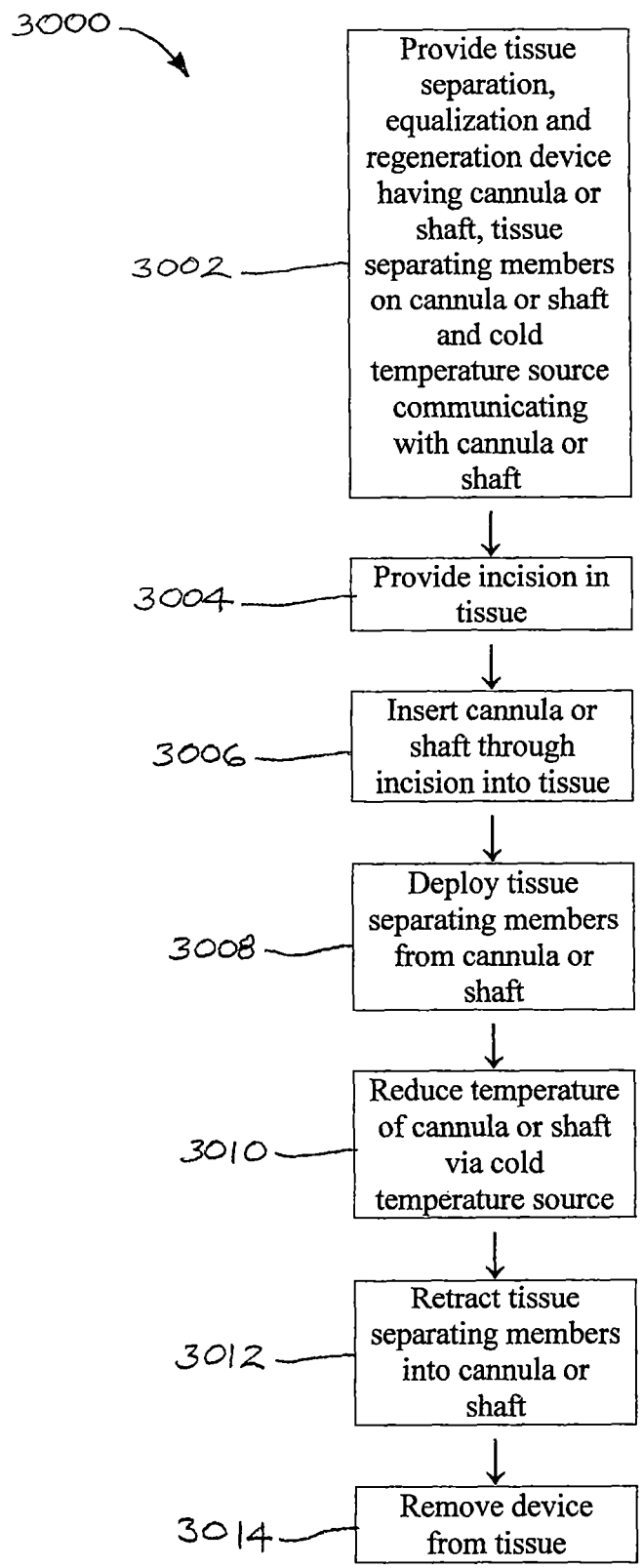
FIG. 30 is a flow diagram of an illustrative embodiment of a tissue separation, equalization and regeneration method.

Referring next to FIG. 30, a flow diagram 3000 of an illustrative embodiment of a tissue separation, equalization and regeneration method is illustrated. In block 3002, a tissue separation, equalization and regeneration device is provided. The device has a tissue insertion member such as a cannula or shaft, tissue separating members on the cannula or shall and a cold temperature source communicating with the cannula or shaft. In some embodiments, the tissue separating members may be selectively expandable from respective openings in the cannula or shaft, In other embodiments, the tissue separating members may be fixed in an expanded configuration on the cannula or shaft. In block 3004, an incision is made in a tissue. In block 3006, the cannula or shaft of the device is inserted through the incision. In block 3008, the tissue separating members may be expanded or deployed from respective openings in the cannula or shall. The tissue separating members separate adipose tissue portions and define a tissue space between the adipose tissue portions. In block 3010, the temperature of the cannula or shall is reduced to a target temperature via the cold temperature source, Accordingly, the cannula or shaft remains in contact with the tissue and induces apoptosis in the tissue. In block 3012, the tissue separating members may be retracted into the cannula or shaft in some embodiments. In block 3014, the device is removed from the tissue.

While illustrative embodiments of the disclosure have been described above, it will be recognized and understood that various modifications can be made in the disclosure and the appended claims are intended to cover all such modifications which may fall within the spirit and scope of the disclosure.

What is claimed is:

1. A method of inducing apoptosis in a tissue, comprising:
providing a device having a cannula including a cannula interior, a plurality of expandable members selectively extendable from the cannula interior and at least one opening communicating with the cannula interior;
providing an incision in tissue;
inserting the cannula of the device through the incision into the tissue;
extending the plurality of expandable members from the cannula interior;
reducing a temperature of the tissue by introducing a temperature reducing fluid from the cannula interior through the at least one opening of the cannula into the tissue, wherein the temperature reducing fluid contacts and induces apoptosis in the tissue; and
removing the cannula from the tissue.

2. The method of claim 1 wherein reducing the temperature of the tissue by introducing the temperature reducing fluid from the cannula interior through the at least one opening of the cannula into the tissue comprises reducing the temperature of the tissue to a temperature of from about −21.12° C. to about 0° C. by introducing the temperature reducing fluid from the cannula interior through the at least one opening of the cannula into the tissue.

3. The method of claim 1 wherein providing the incision in the tissue comprises providing the incision in adipose tissue.

4. The method of claim 1 wherein reducing the temperature of the tissue by introducing the temperature reducing fluid from the cannula interior through the at least one opening of the cannula into the tissue comprises pumping the temperature reducing fluid through the cannula interior of the cannula and through the at least one opening into the tissue.

5. The method of claim 4 wherein pumping the temperature reducing fluid from the cannula interior through the at least one opening of the cannula into the tissue comprises pumping the temperature reducing fluid from the cannula interior through the at least one opening of the cannula into a tissue space between portions of the tissue.

6. The method of claim 5 wherein pumping the temperature reducing fluid from the cannula interior through the at least one opening of the cannula into the tissue space comprises pumping temperature reducing saline solution from the cannula interior through the at least one opening of the cannula into the tissue space.

7. The method of claim 1 wherein providing the device having the cannula including the cannula interior comprises providing the device having the cannula including the cannula interior and at least, one expandable member, disposed in the cannula interior, the at least one expandable member expandable outwardly from the cannula interior upon displacement of the at least one expandable member along a longitudinal axis of the cannula in the cannula interior.

8. The method of claim 7 further comprising separating adjacent portions of the tissue from each other by expanding the at least one expandable member from the cannula interior of the cannula upon displacement of the at least one expandable member alone the longitudinal axis of the cannula in the cannula interior.

9. A method of inducing apoptosis in a tissue, comprising:
providing a device having a generally elongated cannula with a cannula wall enclosing a cannula interior and having a distal cannula end, a plurality of member openings in the cannula wall, a plurality of expandable members in the cannula interior at the plurality of member openings, respectively, and expandable from the cannula interior through the plurality of member openings, respectively, and a temperature reducing fluid source disposed in fluid communication with the cannula interior;
providing an incision in tissue;
inserting the cannula through the incision into the tissue;
separating adjacent portions of the tissue from each other by expanding the plurality of expandable members front the plurality of member openings, respectively;
reducing a temperature of the tissue by pumping a supply of temperature reducing fluid from the temperature reducing fluid source through the cannula interior into the tissue; and
removing the cannula from the tissue.

10. The method of claim 9 wherein pumping the supply of temperature reducing fluid from the temperature reducing fluid source through the cannula interior into the tissue comprises pumping the supply of temperature reducing fluid having a temperature of from about −21.12° C. to about 0° C. from the temperature reducing fluid source through the cannula interior into the tissue.

11. The method of claim 9 wherein providing the incision in tissue comprises providing the incision in adipose tissue.

12. The method of claim 9 further comprising pumping the temperature reducing fluid from the cannula interior of the cannula into a tissue space between the adjacent portions of the tissue.

13. The method of claim 9 wherein pumping the supply of temperature reducing fluid from the temperature reducing fluid source through the cannula interior into the tissue comprises pumping the supply of temperature reducing saline solution from the temperature reducing fluid source through the cannula interior into the tissue.

14. A method of inducing apoptosis in a tissue, comprising:
providing a device having a generally elongated device shaft of solid construction, the device shaft comprising a thermally conductive material and a plurality of expanded members extending outwardly from and in fixed relationship to the device shaft at generally a 90-degree angle with respect to each other around a circumference of the device shaft;
providing an incision in tissue;
inserting the device shaft of the device through the incision into the tissue;
reducing a temperature of the tissue by reducing a temperature of the device shaft; and
removing the device shaft from the tissue.

15. The method of claim 14 wherein reducing the temperature of the device shaft comprises reducing the temperature of the device shaft to a temperature of from about −21.12° C. to about 0° C.

16. The method of claim 14 wherein providing the incision in tissue comprises providing the incision in adipose tissue.

17. The method of claim 14 wherein reducing the temperature of the device shaft comprises reducing the temperature of the device shaft utilizing a source of refrigerant to maintain the device shaft at a reduced temperature via compression and evaporation of the refrigerant.

18. The method of claim 14 wherein providing the generally elongated device shaft comprises providing the generally elongated device shaft with a tapered or sharpened distal shaft end and a diameter of about 2.5 mm or less.

* * * * *